(12) United States Patent
Orii et al.

(10) Patent No.: US 7,711,528 B2
(45) Date of Patent: May 4, 2010

(54) ACCURACY VERIFICATION PROGRAM FOR MODEL PARAMETER COMPUTATION USING A QUANTIFIER ELIMINATION METHOD

(75) Inventors: Shigeo Orii, Kawasaki (JP); Hirokazu Anai, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 365 days.

(21) Appl. No.: 11/237,661

(22) Filed: Sep. 29, 2005

(65) Prior Publication Data

US 2006/0080066 A1    Apr. 13, 2006

(30) Foreign Application Priority Data

Sep. 30, 2004    (JP)    ............................. 2004-288404

(51) Int. Cl.
G06F 7/60    (2006.01)
(52) U.S. Cl. .......................................................... 703/2
(58) Field of Classification Search ...................... 703/2
See application file for complete search history.

(56) References Cited

FOREIGN PATENT DOCUMENTS

JP    2004-38618    2/2004

OTHER PUBLICATIONS

Jirstrand, 1997 Academic Press Limited., Nonlinear Control System Design by Quantifier Elimination. pp. 137-152.*
Basu., 1997 IEEE, An Improved Algorithm for Quantifier Elimination over Real Closed Fields., pp. 56-65.*
Brown., 2003 Japan Society for Symbolic and Algebraic Computation., An Overview of QEPCAD B: a Tool for Real Quantifier Elimination and Formula Simplification. pp. 13-22.*
Yu et al. Nov. 1961., "Functional Analog-To-Digital Converters For AC Transduers of Scanning Control systems", pp. 896-900.*
Ratschan et al. May 11, 2001., http://www.arXiv:cs/0105021v1., Solving Composed First-Order Constraints from Discrete—Time Robust Control. p. 1-11.*
Hermann Georg Holzütter, et al., "SIMFIT: a microcomputer software-toolkit for modelistic studies in biochemistry", *CABIOS*, vol. 6, No. 1, 1990, pp. 23-28.
B. F. Caviness, et al., "Quanitifier Elimination and Cylindrical Algebraic Decomposition", *Texts and Monographs in Symbolic Computation*, SpringerWeinNewYork, 1998, pp.: preface 1, vi-xii, pp. 1-7.
Japanese Office Action issued on Jun. 2, 2009 in corresponding Japanese Patent Application 2004-288404.
Hirokazu Anai, "Control Theory and Computer Algebra", Instrument and Control, The Society of Instrument and Control Engineers, vol. 37, No. 12, pp. 863-869, Dec. 10, 1998.
Hirokazu Anai, Shinji Hara, "Robust Control System Design by Quantifier Elimination", Systems/Control/Information, Institute of Systems, Control, and information Engineers, vol. 44, No. 6, pp. 13-17, Jun. 15, 2000.

(Continued)

*Primary Examiner*—Paul L Rodriguez
*Assistant Examiner*—Eunhee Kim

(57) ABSTRACT

A program causes a computer to perform a step 1 of reading a model from a storage apparatus; a step 2 of computing difference equations by replacing variables with numeric values of a time-series that are stored in the storage apparatus; a step 3 of determining ranges of parameters of the model using a quantifier elimination method and a step 4 of verifying numbers of significant figures that show an accuracy of a computation by the determined ranges of parameters of the model.

10 Claims, 10 Drawing Sheets

OTHER PUBLICATIONS

Hirokazu Anai, "Quantifier elimination—algorithm, implementation and application", Formula Manipulation, Japan Society for Symbolic and Algebraic Computation, vol. 10, No. 1, pp. 3-12, Aug. 2003.

Ming Chen, Ralf Hofestaedt, "Quantitative Petri net model of gene regulated metabolic networks in the cell", in Silicon Biology, vol. 3, pp. 347-365, Mar. 2003.

* cited by examiner

Quantifier Elimination (QE)

Input: first-order formula
- Polynomial equations, inequalities, inequations
- quantifiers [$\exists, \forall$], Boolean operations[$\wedge, \vee, \neg, \Rightarrow$, etc]

Output: an equivalent quantifier-free formula
- Possible regions of unquantified variables as semi-algebraic sets
  ( if all variables are quantified → *true* or *false* )

Example: $\exists x \ ( x^2 + bx + c = 0 ) \quad \underset{QE}{} \quad \underline{b^2 - 4c \geq 0}$

F I G. 2

Constraint Solving via QE

Example1: $\exists x \exists y \ [\ 1 < x < 10 \ \wedge \ y > 0 \ \wedge \ 6xy > 0 \ \wedge \ xy - 2 > 0 \ \wedge$
$(xy - 2)(2 + 4x - 2xy) - 6xy > 0 \ ]$ ⇒ true      Sample value: $(x, y) = (5, 1)$ Example2: $\exists x \ [\ 1 < x < 10 \ \wedge \ y > 0 \ \wedge \ 6xy > 0 \ \wedge \ xy - 2 > 0 \ \wedge$
$(xy - 2)(2 + 4x - 2xy) - 6xy > 0 \ ]$ ⇒ $50y^2 - 100y + 21 < 0 \ \wedge \ y > 0$ i.e. $y \in (0.24, 1.76)$

F I G. 3

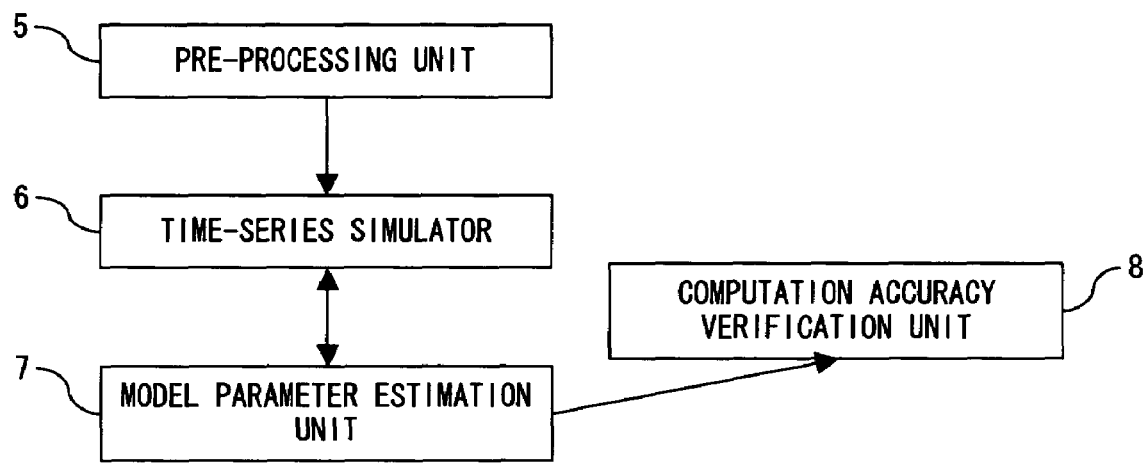
F I G. 4

| | | | | | | | | |
|---|---|---|---|---|---|---|---|---|
| M+M | ⇌ | E | $k_{11}$ | $k_{12}$ | | $v_1 = k_{11}$ [M][M] | − | $k_{12}$ [E] |
| S+E | ⇌ | ES | $k_{21}$ | $k_{22}$ | | $v_2 = k_{21}$ [S][E] | − | $k_{22}$ [ES] |
| ES | → | E+P | $k_3$ | | | $v_3 = k_3$ [ES] | | |
| E+P | ⇌ | EP | $k_{41}$ | $k_{42}$ | | $v_4 = k_{41}$ [E][P] | − | $k_{42}$ [EP] |
| E+I | ⇌ | EI | $k_{51}$ | $k_{52}$ | | $v_5 = k_{51}$ [E][I] | − | $k_{52}$ [EI] |
| EI | → | EJ | $k_6$ | | | $v_6 = k_6$ [EI] | | |

F I G. 6

$k_{11} = 0.1, \quad k_{12} = 1E-4$
$k_{21} = 100, \quad k_{22} = 300$
$k_3 = 10$
$k_{41} = 100, \quad k_{42} = 500$
$k_{51} = 100, \quad k_{52} = 0.1$
$k_6 = 0.1$

| No. | | INPUT NUMBER OF SIGNIFICANT FIGURES | k22 | k3 | k42 | k52 | k6 |
|---|---|---|---|---|---|---|---|
| 1 | INPUT VALUE | — | 313.0 | 10.13 | 382.2 | 1.285e-8 | 1.347e-8 |
| 2 | COMPUTATION VALUE | ELEVEN DIGITS | 312.939266078 ~ 312.939283939 | 10.1907139530054393 ~ 10.1907318280091359 | 382.199999383 ~ 382.200000092 | 4.8527275167 e-7 ~ 0 | 4.8616275945 e-7 ~ 0 |
| 3 | COMPUTATION VALUE | FOUR DIGITS | 312.858794599 ~ 313.068631668 | 10.2934399672229455 ~ 10.5032770229940493 | 382.318787882 ~ 382.327112118 | 0.0055495038 7288 ~ 0 | 0.005549504 91524 ~ 0 |

ACCURACY VERIFICATION PROGRAM FOR MODEL PARAMETER COMPUTATION USING A QUANTIFIER ELIMINATION METHOD

BACKGROUND OF THE INVENTION

1. Field of the Invention

The present invention relates to a fitting method of model parameters in various types of systems that are described in, for example, differential equations. More concretely, the present invention relates to a program that verifies and controls accuracy of model parameter computation using quantifier elimination method.

2. Description of the Related Art

In the analysis of various types of systems described in, for example, ordinary differential equations, a parameter fitting method of fitting the model parameters and the initial values of differential equations is executed in such a way that the observed values of a time-series become equal to the commutated values of the time-series of a differential equation model. For example, in order to clarify the mechanism of a biochemical reaction, a fitting computation is executed in such a way that the observed values of a time-series and the values computed by a differential equation model are the same, thereby estimating model parameters and initial values.

According to this method, in the first step, the time-series computations are executed at first by a differential equation model using suitable model parameters and suitable initial values. In the second step, model parameters and initial values are estimated in such a way that the results of computation and the observed values of a time-series match with each other. In the third step, the time-series computations are executed by a differential equation model using the estimated model parameters and the estimated initial values. Then, the second and third steps are repeated until the sum of squared residuals among the results of the time-series computations and the observed values of a time-series becomes minimum, or equal to a certain threshold value or less.

As a conventional technology of such a parameter fitting method, there is the following document related to the mechanism analysis system of HIV proteinase.

[Nonpatent Literature 1]

Hermann Georg Holzhutter and Alfredo Colosimo; SIMFIT: a microcomputer software-toolkit for modelistic studies in biochemistry, CABIOS Vol. 6, No. 1, pp. 23-28 (1990) (http://www.gepasi.org/gep3tuts.html.)

In this literature, the following steps are executed.

(1) Time-series simulations are executed by a simulator using suitable initial values and suitable initial parameters.

(2) In order to match the results of the simulation with the experimental values, a weighted sum of squared residuals is computed using observed values, the results of simulation and model parameter values by a minimizer and then model parameters are computed in such a way that the computed sum becomes minimum.

(3) Time-series simulations are executed by the simulator using the computed model parameters. At this time, initial values are changed so that the initial values such that the weighted sum of squared residuals computed by the minimizer becomes minimum are detected.

(4) Time-series simulations are executed by the simulator using the model parameters computed in (2) and the initial values detected in (3).

(5) A weighted sum of squared residuals is computed by the minimizer using the observed values, the simulation results and the model parameters and then model parameters for minimizing the value are obtained.

(6) Returning to (2) until the model parameters and the initial values converge up to the predetermined range. In this way, the accuracies of the values of model parameters that are obtained by a fitting computation is discussed using statistic data such as a sum of squared residuals in the conventional technology. Therefore, in the conventional fitting computation, the influence caused by the difference between the accuracy of the time-series computations and that of a fitting computation or the fluctuation among observations is present. Accordingly, there arises a problem such that the accuracy of model parameters or that of initial values that are obtained by the fitting computation cannot be correctly discussed. That is, according to the conventional method, there are the following problems. Firstly, it cannot be distinguished whether the standard deviation of model parameters that is obtained by fitting the observed values of a time-series and the differential equation model is generated by an experimental error or a numerical calculation. Therefore, the accuracy of the obtained values of parameters cannot be discussed. Furthermore, there is no method of easily clarifying the factors of computation accuracy or controlling the accuracy.

SUMMARY OF THE INVENTION

The present invention aims at verifying the accuracy of a model parameter computation.

In one of the preferred embodiments of the present invention, it is assumed that a storage medium for storing a program to verify the computation accuracy of model parameters is used. In this program, a model represented by difference equations is read in from a storage apparatus and variables of the read-in model are replaced with the numeric values of a time-series that are stored in the storage medium, thereby computing difference equations that use the numeric values of a time-series. Then, the ranges of the model parameters are determined by applying a quantifier elimination method to each of the difference equations. Then, the numbers of significant figures that show the accuracy of a model parameter computation are verified by the ranges of the determined model parameters.

In this way, the quantifier elimination method is applied to, for example, the fitting computation of the model parameters, and the accuracy of a computation of the model parameters can be verified by the range of numeric values of the model parameters that are obtained as a result. At the same time, the accuracy can be controlled by adjusting, for example, the significant figures of numeric values of model variables or by changing a numerical solving method of difference equations, in order to improve the approximateness of a difference equation model.

BRIEF DESCRIPTION OF THE DRAWINGS

FIG. 2 explains the outline of a quantifier elimination (QE) method;

FIG. 3 shows an application example of the QE method for a constraint problem;

FIG. 4 is a block diagram showing a whole accuracy verification system for model parameter computation;

FIG. 6 explains the mechanism of HIV proteinase;

FIG. 7 shows an example of values of the model parameters in respect of FIG. 6;

FIG. 8 explains the influence of the numbers of significant figures of input data in respect of the accuracy of a model parameter computation;

DESCRIPTION OF THE PREFERRED EMBODIMENTS

Figure 1:
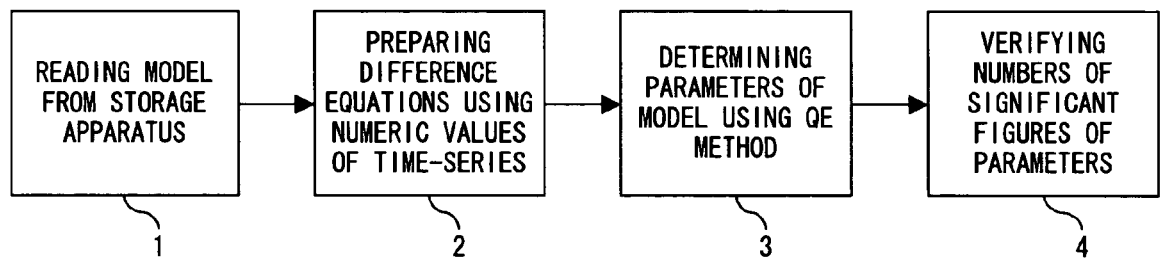
FIG. 1 is a principle block diagram showing the function of an accuracy verification program for model parameter computation of the present invention.

FIG. 1 is a principle block diagram showing the function of an accuracy verification program for model parameter computation of the present invention. FIG. 1 shows a program to be used by the computer for estimating model parameters. In step 1, a model represented by difference equations is read in from a storage apparatus. In step 2, variables of the model are replaced with the numeric values of a time-series that are stored in the storage apparatus and then computations of the difference equations that use the numeric values of a time-series are executed. In step 3, the ranges of parameters of the model are determined using a quantifier elimination (QE) method. In step 4, the numbers of significant figures that show the computation accuracy of the parameters are verified by the determined ranges of the model parameters.

According to an embodiment of the present invention, when the computation accuracy of model parameters is verified low based on the verification of the numbers of significant figures in step 4 of FIG. 1, the steps in and after step 1 of reading a model can be repeated after a processing for the enhancement of the computation accuracy is executed. In this case, the processing for the enhancement of computation accuracy can include the adjustment of the numbers of significant figures of numeric values of input data including variables or the change of numerical solving methods of differential equations.

In an embodiment, numeric values at two times can be used as the above-mentioned numeric values of a time-series or each of the above-mentioned difference equations can include an error variable corresponding to each of the difference equations in addition to parameters of the model.

An accuracy verification program for model parameter computation of the present invention causes a computer to execute a step of reading the model represented by difference equations from a storage apparatus; a step of replacing variables of the model with the numeric values of a time-series that are stored in the storage apparatus, thereby computing the difference equations that use the numeric values of a time-series; a step of determining parameters of the model using a quantifier elimination method; a step of comparing the determined model parameters with model parameter input values of the read model, thereby verifying whether or not the accuracy of the determined model parameters falls within a predetermined accuracy range; and a step of repeating processes in and after the above-mentioned reading step after executing a processing of enhancing the accuracy when the accuracy range does not fall within the predetermined accuracy range according to the verification results.

According to an embodiment of the present invention, the processing for the enhancement of accuracy includes an adjustment of the numbers of significant figures of a numeric value of input data including variables or the change of numerical solving methods of differential equations.

Furthermore, in the present invention, the target of computation accuracy verification is not limited to model parameters so that model variable values can be also the target. In addition, this processing can be also applied to the estimation of model variable values. In this case, a specific value is given to each of all the model parameters and the model variables at a certain time t, and the values of model variables at a time t+Δt are determined using a QE method, thereby executing the verification of the computation accuracy. In an embodiment, it is possible to use a computer-readable portable storage medium for storing an accuracy verification program for model parameter computation in the present invention, an accuracy verification method for model parameter computation corresponding to this program or an accuracy verification apparatus for model parameter computation for realizing such an accuracy verification system for model parameter computation.

According to the present invention, by applying a quantifier elimination (QE) method, it becomes possible to verify the computation accuracy of model parameters only by looking at the ranges of model parameters to be discussed, that is, the numbers of significant figures, when the fitting computation of model parameters is executed to clarify, for example, the mechanism of a biochemical reaction. Therefore, the outline of this QE method is firstly explained.

Many industrial problems or mathematical problems are described as a formula including equations, inequalities, quantifiers, the Boolean operations, etc. Such formula is called first-order formula. An algorithm of a quantifier elimination (QE) method is the algorithm for configuring an equivalent quantifier-free formula based on the given first-order formula.

The following document introduces the outline of this quantifier elimination method.

[Nonpatent Literature 2]

Hirokazu Anai [Quantifier Elimination-algorithm•implementaion•application-] Journal of Japan Society of Symbolic Algebraic Computation, Vol. 10, No. 1, pp. 3-12 (2003)

FIG. 2 explains the outline of this QE method. In this drawing, an input is a first-order formula using polynomial equations or inequalities while an output is a feasible region of a parameter without a quantifier. In the case where all the variables are quantified, it can be determined whether the problem is true or false, that is, whether the solution is present or not. In the case where the solution is present, the solution of a sample can be obtained as an output. Such a problem is deemed as a decision problem.

In FIG. 2, in respect of a quantified problem such that a variable X should satisfy a formula of $X^2+bX+c=0$, a formula such as $b^2-4c>=0$ is obtained as an equivalent quantifier-free formula.

In the case where quantifiers are not present in respect of some variables, a quantifier-free formula that is equivalent to the first-order formula can be obtained by a QE algorithm. The thus-obtained formula shows the possible regions of the remaining quantifier-free variables. In the case where such a region is not present, false is outputted. This problem is called a general qualifier elimination problem.

FIG. 3 explains an application example of this quantifier elimination method to the solution of a specific constraint problem. Since quantifiers are attached to both x and y in the example 1, "true" and the sample solution are outputted via a QE algorithm. In the example 2, since a quantifier is attached to only x, a feasible range of y that is the other variable is outputted via the QE algorithm.

In a present embodiment, the accuracy verification for model parameter computation or a parameter fitting computation is executed as a whole in accordance with the following steps in the system of FIG. 4. At first, a pre-processing unit 5 inputs each data and adjusts the number of significant digits in respect of computation or selects a numerical solving method of each of differential equations, for example, the Euler method. Then, a time-series simulator 6 runs a simulation. Corresponding to the results of the simulation, a model parameter estimation unit 7 estimates model parameters in such a way that computation results of the simulation and observed results match with each other. Then, the results are given to a computation accuracy verification unit 8 and the verification results by the computation accuracy verification unit 8 are given to the time-series simulator 6 if necessary. Accordingly, in the present embodiment, the most characteristic processing is executed by the computation accuracy verification unit 8.

Figure 5:
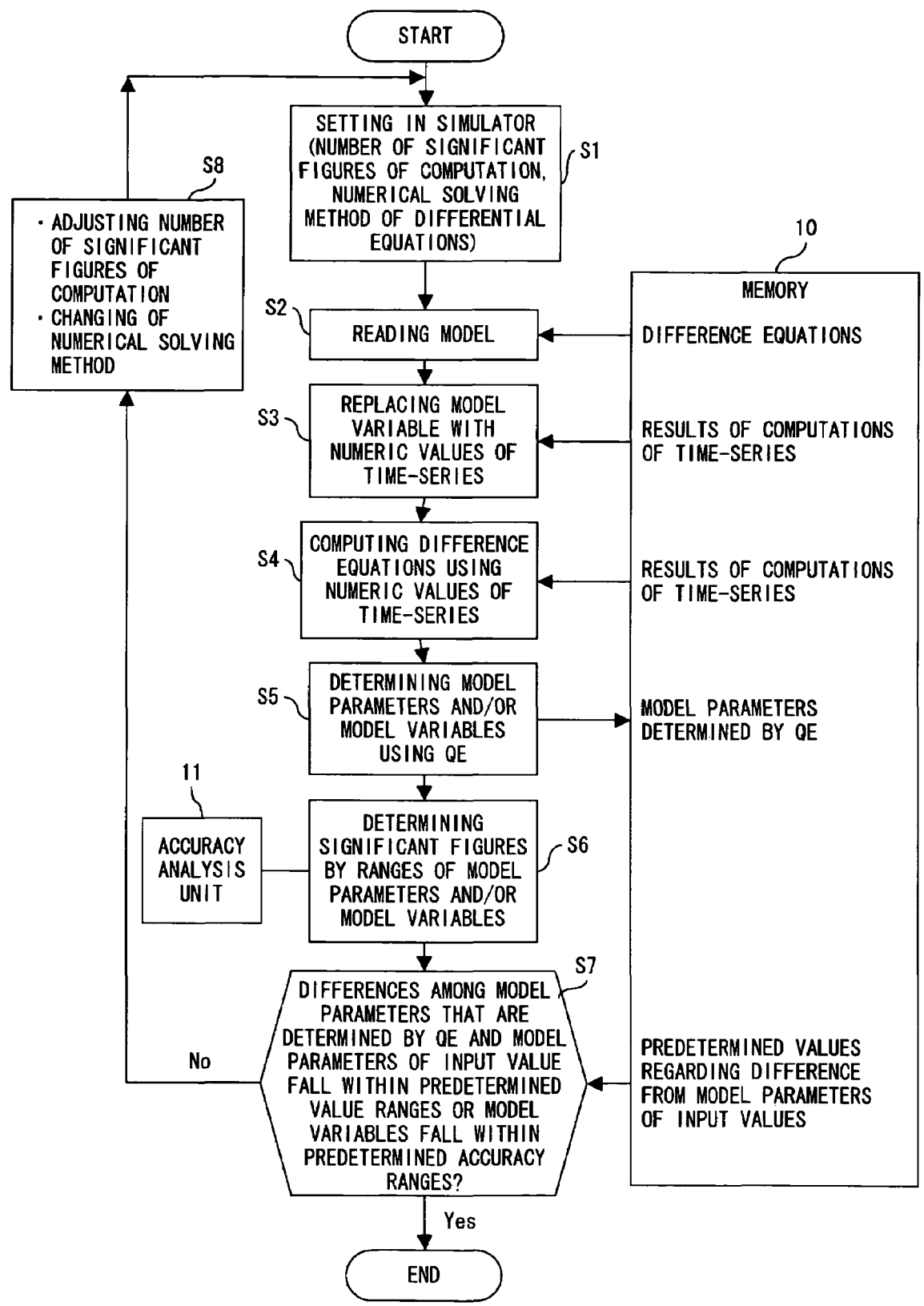
FIG. 5 is a detailed flowchart of an accuracy verification processing for model parameter computation according to the present preferred embodiments.

The following is the detailed explanation of the accuracy verification method for model parameter computation using a QE method. According to this method, the accuracy verification for model variable value computation can be executed as well as the accuracy verification for model parameter computation. FIG. 5 shows a detailed flowchart of accuracy verification processes for model parameter computation in the present embodiment. In FIG. 5, in step S1, the number of significant figures of a computation and the numerical solving method of differential equations are given to a simulator. When a processing starts, these values are suitably set. Then, in step S2, difference equations, etc. are read in from a memory 10 as models. In step S3, the variables of a model are replaced with numeric values of a time-series using the time-series computation results in the memory 10. In step S4, the computation of difference equations that use the numeric value of a time-series is executed using the time-series computation results stored in the memory 10.

Subsequently, in step S5, the determination processing of model parameters and/or model variables is executed using a QE algorithm. In respect of this QE algorithm, the variables of a model are replaced with the numeric values of a time-series, that is, the values of dynamics in steps S3 and S4. Furthermore, specific numeric values are given to the corresponding model parameters that are not the targets of computation accuracy verification among model parameters. For example, the ranges of model parameters to be the targets of computation accuracy verification are determined by attaching a quantifier only to an error variable that corresponds to each difference equation, which is described later and the thus-determined model parameters are stored in the memory 10.

Subsequently, by the ranges of model parameters and/or model variables that are determined by the QE algorithm, in step S6, the numbers of significant figures are determined when the model parameters are computed and then an accuracy analysis unit 11 analyzes the computation accuracy. In the case where only the computation accuracy of the model parameters is verified, it is possible that the processes terminate in step S6. However, in the case where it is determined whether or not the difference among the model parameters that are determined by the QE algorithm and the model parameters of input values falls within the predetermined range, it is determined in step S7 whether or not this difference falls within the predetermined range or the model variables fall within the predetermined accuracy range. In the case where this difference falls within the predetermined range, the processes terminate immediately. In the case where the difference does not fall within the predetermined range, however, the number of significant digits in respect of a computation is adjusted and/or the numerical solving method of differential equations is changed, for example, from the Euler method to the Runge-Kutta method, thereby repeating the processes in and after step S1. Then, in the case where it is determined in step S7 that the difference among the model parameters that are determined by the QE algorithm and the model parameters of the input value falls within the predetermined range, processes terminate. Otherwise, in the case where it is determined in step S6 that the accuracy is lacking by the verification of the numbers of significant figures in respect of the model parameters determined by the QE algorithm as mentioned-above, it is possible that the processes in and after step S8 are executed without executing the processing in step S7.

The following is further explanation of the accuracy verification for model parameters computation, using specific examples. FIG. 6 explains the mechanism of the biochemical reaction of HIV proteinase. In the same drawing, E indicates proteinase and this E causes the HIV to develop. I indicates an inhibitor of HIV. P indicates the virus protein of developing HIV while S indicates the precursor protein (substrate). In the case where E exists separately, it becomes equilibrium with M.

In FIG. 6, for example, in the top reaction formula the reaction velocity $v_1$ is determined by both a coefficient $k_{11}$ for determining the velocity in the right direction and a coefficient $k_{12}$ for determining the velocity in the left direction. Among these enzymes, the proteinase E and the precursor protein S are positive at the time of t=0 because a reaction cannot start in the case that they are 0 at the time of t=0. The inhibitor I is externally given and the virus protein P, etc. can be 0 at the time of t=0.

In the model of FIG. 6, ten coefficients from $k_{11}$ to $k_6$ for determining each reaction velocity of the respective reaction formulas are model parameters. The initial values set in the fitting computation are given in FIG. 7. However, among these parameters, five coefficients such as $k_{22}$, $k_3$, $k_{42}$, $k_{52}$ and $k_6$ are determination target model parameters in the QE algorithm so that the QE algorithm is executed without using these values.

The model is represented by the following ordinary differential equations using the reaction velocities from $v_1$ to $v_6$ of the respective reaction formulas shown in FIG. 6.

$$\frac{d[M]}{dt} = -2 \cdot v_1$$

$$\frac{d[E]}{dt} = v_1 - v_2 + v_3 - v_4 - v_5$$

$$\frac{d[S]}{dt} = -v_2$$

$$\frac{d[ES]}{dt} = v_2 - v_3$$

$$\frac{d[P]}{dt} = v_3 - v_4$$

$$\frac{d[EP]}{dt} = v_4$$

$$\frac{d[I]}{dt} = -v_5$$

$$\frac{d[EI]}{dt} = v_5 - v_6$$

$$\frac{d[EJ]}{dt} = v_6$$

The following are constraints based on these differential equation.

$\phi_1$(M,E,S,ES,P,EP,I,EI,EJ,JM,JE,JS,JES,JP,JEP,JI, JEI,JEJ,k22,k3,k42,k52,k6,erm,ere,ers,eres,erp, erep,eri,erei,erej,emax)=erm+JM+2*(1/ 10*M*M−1/10000*E)=0 and ere+JE−((1/10*M*M−1/10000*E)−(100*S*E− k22*ES)+(k3*ES)−(100*E*P−k42*EP)− (100*E*I−k52*EI))=0 and ers+JS+(100*S*E−k22*ES)=0 and eres+JES−((100*S*E−k22*ES)−(k3*ES))=0 and erp+JP−((k3*ES)−(100*E*P−k42*EP))=0 and erep+JEP−(100*E*P−k42*EP)=0 and eri+JI+(100*E*I−k52*EI)=0 and erei+JEI−((100*E*I−k52*EI)−k6*EI)=0 and erej+JEJ−k6*EI=0 and M>=0 and E>0 and S>0 and ES>=0 and P>=0 and EP>=0 and I>=0 and EI>=0 and EJ>=0 and k22>0 and k3>0 and k42>0 and k52>0 and k6>0 and −emax<erm<emax and −emax<ere<emax and −emax<ers<emax and −emax<eres<emax and −emax<erp<emax and −emax<erep<emax and −emax<eri<emax and −emax<erei<emax and −emax<erej<emax and emax>=0

Here, the constraints from the top to the ninth are obtained by replacing derivatives of above-mentioned differential equations as variables, for example, JM indicates dM/dt and substituting values to five parameters among ten parameters of FIG. 7. Generally, in the case where data obtained by simulations using numeric values or experiments are used as the values of variables, an error in numerical computation or an observation error is included. Therefore, if a solution is actually present, the result sometimes suggests that there is no solution in QE algorithm that executes an exact computation by symbolic computation. Consequently, in the present embodiment, it is assumed that a minor error is included in the computed value of each difference equation and each of difference equations is prepared using variables of the error, thereby applying a QE method. Actually, constraints including error terms are prepared using nine variables such as erm, ere, ers, eres, erp, erep, eri, erei and erej that are obtained by adding er at the heads of respective variables, as error variables for the constraints. An equation $\phi 1$ is obtained by adding to these constraints both an inequality equation for giving physical limitations to each variable and each model parameter, and each of inequality equations such that a maximum value of the absolute value of each error term is set emax.

The following $\phi 2$ is obtained by substituting variable valuse (dynamics) at the time of t=3500 seconds and by computing JM, JE, JS, JES, JP, JPE, JI, JEI, and JEJ by Eular's method using variable valuses at the time of t=3500 seconds and t=3512 seconds for the equation $\phi 1$.

$\phi_2$(k22,k3,k42,k52,k6,erm,ere,ers,eres,erp,erep,eri, erei,erej,emax)=erm+54570530533/ 10000000000000000000+2*(1/10*2083207137/ 10000000000000*2083207137/ 10000000000000−1/10000*15805096851/ 50000000000000)=0 and ere+(−19873341333)/10000000000000000000−((1/ 10*2083207137/10000000000000*2083207137/ 10000000000000−1/10000*15805096851/ 50000000000000)−(100*81107993833/ 100000000000*15805096851/50000000000000− k22*15868828653/200000000000000)+ (k3*15868828653/200000000000000)− (100*15805096851/ 50000000000000*24186840323/1000000000− k42*4000788351/2000000000000)− (100*15805096851/ 50000000000000*60962355629/ 10000000000000000000−k52*7499638667/ 5000000000000))=0 and ers+(−80849528891)/100000000000000+ (100*81107993833/ 100000000000*15805096851/50000000000000− k22*15868828653/200000000000000)=0 and eres+(−497475643)/6250000000000000− ((100*81107993833/ 100000000000*15805096851/50000000000000− k22*15868828653/200000000000000)− (k3*15868828653/200000000000000))=0 and erp+64681647/80000000000−((k3*15868828653/ 200000000000000)−(100*15805096851/ 50000000000000*24186840323/1000000000− k42*4000788351/2000000000000)=0 and erep+108596351/2000000000000000− (100*15805096851/ 50000000000000*24186840323/1000000000− k42*4000788351/2000000000000)=0 and eri+74795879/20000000000000000000000+ (100*15805096851/ 50000000000000*60962355629/ 10000000000000000000−k52*7499638667/ 5000000000000)=0 and erei+(−4122550001)/200000000000000000000− ((100*15805096851/ 50000000000000*60962355629/ 10000000000000000000−k52*7499638667/ 5000000000000)−k6*7499638667/ 5000000000000)=0 and erej+10304502923/500000000000000000000− k6*7499638667/5000000000000=0 and k22>0 and k3>0 and k42>0 and k52>0 and k6>0 and −emax<erm<emax and −emax<ere<emax and −emax<ers<emax and −emax<eres<emax and −emax<erp<emax and $-emax<erep<emax$ and $-emax<eri<emax$ and $-emax<erei<emax$ and $-emax<erej<emax$ Before unknown parameters are determined by a QE method, a maximum value emax of the absolute value of an error term in each of the above-mentioned equations is determined. This process corresponds to the solving of a QE problem such as $\chi=\exists k22\ \exists k3\ k42\ \exists k52\ \exists k6\ \exists erm\ \exists ere\ \exists ers\ \exists eres\ \exists erp\ \exists erep\ \exists eri\ \exists erei\ \exists erej\ (\phi2)$. The following $\phi3$ is obtained by substituting the obtained value of emax to $\phi2$.

$\phi3(k22,k3,k42,k52,k6,erm,ere,ers,eres,erp,erep,eri,$
  $erei,erej)=erm+54570530533/$
  $100000000000000000+2*(1/10*2083207137/$
  $10000000000000*2083207137/$
  $10000000000000-1/10000*15805096851/$
  $50000000000000)=0$ and $ere+(-19873341333)/100000000000000000-((1/$
  $10*2083207137/10000000000000*2083207137/$
  $10000000000000-1/10000*15805096851/$
  $50000000000000)-(100*81107993833/$
  $100000000000*15805096851/50000000000000-$
  $k22*15868828653/200000000000000)+$
  $(k3*15868828653/200000000000000)-$
  $(100*15805096851/$
  $50000000000000*24186840323/1000000000-$
  $k42*4000788351/2000000000000)-$
  $(100*15805096851/$
  $50000000000000*60962355629/$
  $1000000000000000000-k52*7499638667/$
  $5000000000000))=0$ and $ers+(-80849528891)/100000000000000+$
  $(100*81107993833/$
  $100000000000*15805096851/50000000000000-$
  $k22*15868828653/200000000000000)=0$ and $eres+(-497475643)/6250000000000000-$
  $((100*81107993833/$
  $100000000000*15805096851/50000000000000-$
  $k22*15868828653/200000000000000)-$
  $(k3*15868828653/200000000000000))=0$ and $erp+64681647/80000000000-((k3*15868828653/$
  $200000000000000)-(100*15805096851/$
  $50000000000000*24186840323/1000000000-$
  $k42*4000788351/2000000000000))=0$ and $erep+108596351/2000000000000000-$
  $(100*15805096851/$
  $50000000000000*24186840323/1000000000-$
  $k42*4000788351/2000000000000)=0$ and $eri+74795879/20000000000000000000000+$
  $(100*15805096851/$
  $50000000000000*60962355629/$
  $1000000000000000000-k52*7499638667/$
  $5000000000000)=0$ and $erei+(-4122550001)/2000000000000000000000-$
  $((100*15805096851/$
  $50000000000000*60962355629/$
  $1000000000000000000-k52*7499638667/$
  $5000000000000)-k6*7499638667/$
  $5000000000000)=0$ and $erej+10304502923/500000000000000000-$
  $k6*7499638667/5000000000000=0$ and $k22>0$ and $k3>0$ and $k42>0$ and $k52>0$ and $k6>0$ and $-2964709/100000000000000000<erm<2964709/$
  $100000000000000000$ and $-2964709/100000000000000000<ere<2964709/$
  $100000000000000000$ and $-2964709/100000000000000000<ers<2964709/$
  $100000000000000000$ and $-2964709/100000000000000000<eres<2964709/$
  $100000000000000000$ and $-2964709/100000000000000000<erp<2964709/$
  $100000000000000000$ and $-2964709/100000000000000000<erep<2964709/$
  $100000000000000000$ and $-2964709/100000000000000000<eri<2964709/$
  $100000000000000000$ and $-2964709/100000000000000000<erei<2964709/$
  $1000000000000000$ and $-2964709/100000000000000000<erej<2964709/$
  $100000000000000000$ A QE method is applied to this $\phi3$ and nine error terms are eliminated, thereby obtaining unknown parameters k22, k3, k42, k52 and k6. These model parameters are constant in terms of time and the obtained values can be compared with the input values. Since this QE computation does not include observed values, the range of the obtained value corresponds to a computation error. The computation error depends on some factors such as the underflow caused by the computation of velocity, the accuracy of d*/dt approximation, the integration error caused by the time-series computations, etc.

The QE problem to be solved is given by the following equation.

$$\tau=\exists erm\exists ere\exists ers\exists eres\exists erp\exists erep\exists eri\exists erei\exists erej \qquad (\phi3)$$

FIG. 8 shows the computation results of the five model parameters determined by the above-mentioned QE algorithm. In this drawing, No. 1 indicates the model parameter of the input value. No. 2 indicates the determination results of the model parameters in the case where the number of significant figures of the input dynamic data is set eleven in the above-mentioned QE algorithm. When the results of No. 2 and the input value of No. 1 are compared, higher four digits of both values are the same in respect of the parameters k22 and k42 while higher three digits of both values are the same in respect of the parameter k3.

No. 3 shows the determination results of the model parameters in the case where the number of significant figures of dynamic data is set four in the QE algorithm. When the results of No. 3 are compared with the input values of No. 1, higher two digits of both values are the same in respect of k22 and k3, and three digits in respect of k42. Therefore, the number of significant figures of input dynamic data necessary for the matching of higher two digits of both values is four. Furthermore, if the matching of higher four digits of both values is required, the necessary number of digits of significant figures is present between four digits to eleven digits.

When only No. 2 is considered, the determined range of k22 is seven digits and the determined range in respect of k3 is six digits while that in respect of k42 is nine digits. Therefore, it can be estimated that the differences among these parameters and No. 1 as input values are generated by factors other than the significant figures of the input dynamic data.

On the other hand, the decision results of the two remaining parameters k52 and k6 change in accordance with the number of significant figures of input dynamic data. Therefore, it can be estimated that the number of significant figures of input dynamic data are lacking for these parameters. Accordingly, it can be understood that in the case where the values of two parameters such as k52 and k6 are important, the number of digits equal to or greater than eleven is required as the number of significant figures of input dynamic data.

In this way, in the present embodiment, the accuracy of model parameters computation can be controlled from the viewpoint of the number of digits of input dynamic data. Furthermore, the contribution of the computation accuracy of the values of JM, JE, JS, JES, JP, JPE, JI, JEI, and JEJ can be discussed in the convergence condition of values like No. 2, for example, by changing Euler's method to another method in respect of the computation method of the derivatives. In addition, if observed values are used as input dynamic data in respect of the computation of No. 2, it is understood that the ranges of decision results obtained by a QE algorithm are almost based on the fluctuation of observation. In this way, in the present embodiment, the analysis and control of computation accuracy can be executed by separating the factors that contributes to the computation accuracy of a model parameter.

As mentioned above, the verification of the accuracy of model parameters computation using a QE algorithm, the control of the computation accuracy, and the comparison with input parameter values, etc. are described in detail. The computation accuracy verification method of the present preferred embodiments can be applied not only to model parameters but also to the variables of a model.

In the accuracy verification for model parameters computation, after a specific numeric value is given to each of parameters other than unknown parameters that are targets of computation accuracy verification among model parameters and the values of dynamics at two times are substituted to difference equations as the values of model variables, unknown parameters are decided using a QE method. In order to verify the computation accuracies of the values of model variables, specific values are given to all the model parameters and at the same time, the model variables at one time t are replaced with the numeric values of a time-series. Then, by applying a QE method, model variable values at the other time of the two times, for example, t+Δt are determined and the computation accuracy is verified by the numbers of significant figures using the range of the model variable values.

Figure 9:
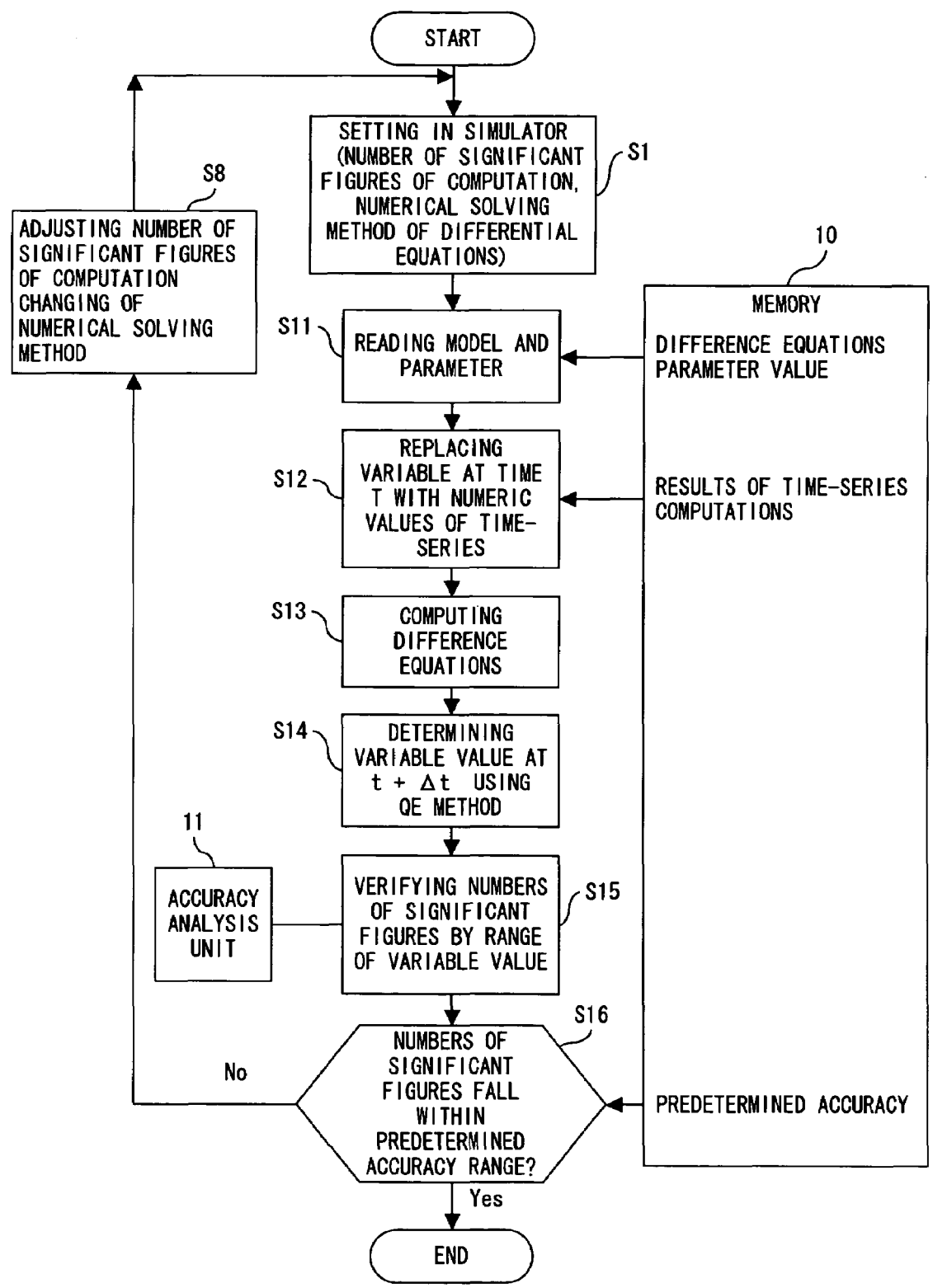
FIG. 9 is a detailed flowchart of an accuracy verification processing for model variable computation according to the present preferred embodiments.

FIG. 9 shows a detailed flowchart of accuracy verification processes for model variable computation. FIG. 9 is similar to FIG. 5 that shows a flowchart of accuracy verification processes for model parameter computation. Here, only the different processes are explained. When processing starts, the same processing that is identical to that of FIG. 5 is executed in step S1. Then, in step S11, the reading of a model that is represented by difference equations and the values of parameters from the memory 10 is executed. In step S12, the model variables at one time t are replaced with the numeric values of a time-series. In step S13, the difference equations are computed. In step S14, the values of model variables at the other time, that is, t+Δt are determined using a QE method. In step S15, the numbers of significant figures are verified by the ranges of the values of model variables determined by the accuracy analysis unit 11. In step S16, the verification results are compared with, for example, a set accuracy range that is stored in advance in the memory 10. In the case where the determined numbers of significant figures fall within the accuracy range, the processes immediately terminate. In the case where the determined numbers of significant figures do not fall within the accuracy range, the processes in and after S1 are repeated after the same processing that is identical to that in step S8 of FIG. 5 is executed.

The major characteristic of the present embodiments is such that in the case where not only a single model parameter and a single model variable but also a plurality of model parameters and that of model variables are verification targets, the ranges of the model parameters and model variables can be determined by only one computation using a QE method. According to a general conventional computation using a numeric value, for example, only one parameter can be determined. In this embodiment, however, for example, the computation accuracies of a plurality of model parameters can be verified by symbolic computation using the numeric values of a time-series.

Figure 10:
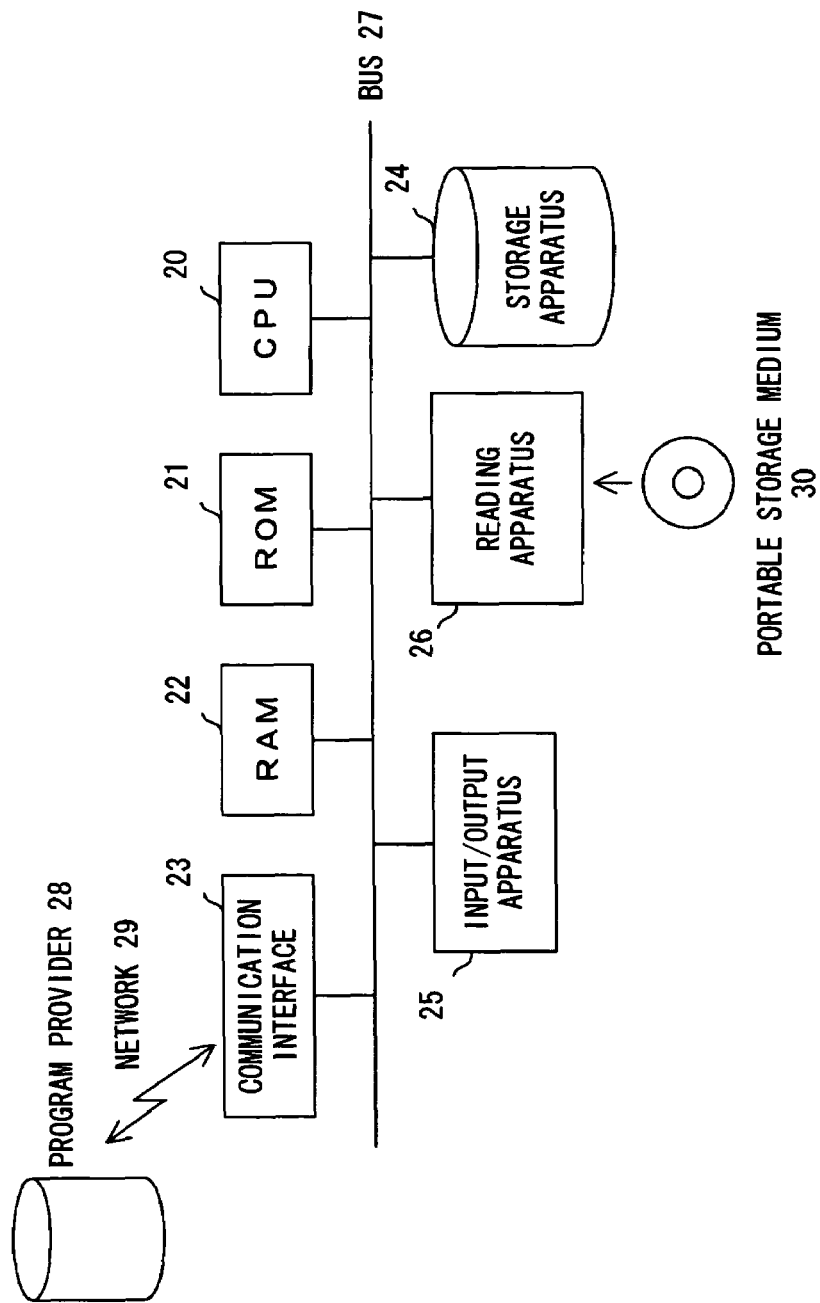
FIG. 10 explains an operation of loading a program for realizing the present invention into a computer.

As mentioned above, a model parameter accuracy verification method of the present invention is explained in detail. It is natural that this accuracy verification method can be realized by a general computer system provided with the software for solving ordinary differential equations. FIG. 10 is a configuration block diagram of such a computer system, that is, a hardware environment.

In FIG. 10, a computer system includes a central processing unit (CPU) 20, a read only memory (ROM) 21, a random access memory (RAM) 22, a communication interface 23, a storage apparatus 24, an input/output apparatus 25, a reading apparatus 26 for a portable storage medium and a bus 27 for connecting all of them.

As the storage apparatus 24, various types of storage apparatuses such as a hard disk, a magnetic disk, etc. can be used. In the storage apparatus 24 and the ROM 21, the programs shown in flowcharts of FIGS. 5 and 9 or the programs as defined in claims of "what is claimed is" of the present invention are stored. By executing these programs using the CPU 20, the accuracy verification for model parameter computation, the fitting computation of parameters by the comparison with an input model parameter, etc. of the present preferred embodiments become possible.

It is possible that these programs are stored in, for example, the storage apparatus 24 from a program provider 28 via a network 29 and the communication interface 23. In addition, it is also possible that these programs are available to the market, are stored in a portable storage medium 30, are set in the reading apparatus 26 and are executed by the CPU 20. As the portable storage medium 30, various types of storage media such as a CD-ROM, a flexible disk, an optical disk, a magnetooptical disk, a DVD, etc. can be used. The programs stored in these storage media are read by the reading apparatus 26 so that the control of a model parameter computation accuracy of the present preferred embodiments, etc. becomes possible.

What is claimed is:

1. A computer-readable storage medium storing a program for verifying an accuracy for model parameters computation, wherein the program causes a computer to perform a process comprising:

reading a model represented by difference equations from a storage apparatus;

computing difference equations that use numeric values of a time-series by replacing variables of the model with numeric values of a time-series that are stored in the storage apparatus;

preparing first constraint equations by implementing, to the difference equations using the numeric values of a time-series, error variables corresponding to the difference equations;

preparing second constraint equations including inequality equations in which a maximum value of an absolute value of each of the implemented error variables is set as an emax value;

determining the emax value by applying a quantifier elimination method to constraint equations including the first and the second constraint equations;

obtaining third constraint equations by substituting the emax value into the second constraint equation;

determining ranges of parameters of the model by applying a quantifier elimination method to constraint equations including the first and the third constraint equations;

verifying numbers of significant figures that show a degree of computation accuracy of model parameters by the determined ranges of parameters of the model; and upon a degree of computation accuracy of the model parameters being verified as less than a predetermined degree by the verification of numbers of significant figures, repeating operations in and after the reading the model after executing a processing of enhancing the degree of computation accuracy, wherein the processing of enhancing the degree of computation accuracy is an adjustment of numbers of significant figures of numeric values of input data including variables.

2. The storage medium storing a program according to claim 1, wherein numeric values observed at two times are used as the numeric values of a time-series.

3. The storage medium storing a program according to claim 1, wherein the difference equations include error variables corresponding to the difference equations in addition to parameters of the model.

4. A computer-readable storage medium storing a program for verifying an accuracy for model parameters computation, wherein the program causes a computer to perform a process comprising:

reading a model represented by difference equations from a storage apparatus;

computing difference equations that use numeric values of a time-series by replacing variables of the model with numeric values of a time-series that are stored in the storage apparatus;

preparing first constraint equations by implementing, to the difference equations using the numeric values of a time-series, error variables corresponding to the difference equations;

preparing second constraint equations including inequality equations in which a maximum value of an absolute value of each of the implemented error variables is set as an emax value;

determining the emax value by applying a quantifier elimination method to constraint equations including the first and the second constraint equations;

obtaining third constraint equations by substituting the emax value into the second constraint equations;

determining ranges of parameters of the model by applying a quantifier elimination method to constraint equations including the first and the third constraint equations;

verifying numbers of significant figures that show a degree of computation accuracy of model parameters by the determined ranges of parameters of the model; and upon a degree of computation accuracy of the model parameters being verified as less than a predetermined degree by the verification of numbers of significant figures, repeating operations in and after the reading the model after executing a processing of enhancing the degree of computation accuracy, wherein the processing of enhancing the degree of computation accuracy is a change of numerical solving methods of differential equations.

5. A computer-readable storage medium storing a program for verifying an accuracy for model parameters computation, wherein the program causes a computer to perform a process comprising:

reading a model represented by difference equations from a storage apparatus;

computing difference equations that use numeric values of a time-series by replacing variables of the model with numeric values of a time-series that are stored in the storage apparatus;

preparing first constraint equations by implementing, to the difference equations using the numeric values of a time-series, error variables corresponding to the difference equations;

preparing second constraint equations including inequality equations in which a maximum value of an absolute value of each of the implemented error variables is set as an emax value;

determining the emax value by applying a quantifier elimination method to constraint equations including the first and the second constraint equations;

obtaining third constraint equations by substituting the emax value into the second constraint equations;

determining ranges of parameters of the model by applying a quantifier elimination method to constraint equations including the first and the third constraint equation;

comparing the determined ranges of parameters of the model with model parameter input values of the read model and verifying whether the determined ranges fall within a predetermined range of a degree of accuracy; and upon the ranges not failing within the accuracy range according to the verification result, repeating the reading the model, the computing difference equations, the preparing the first constraint equations, the preparing the second constraint equations, the determining the emax value, the obtaining third constraint equations, the determining ranges of parameters, and the comparing the range of parameter after executing a processing of enhancing a degree of computation accuracy, wherein the processing of enhancing the degree of computation accuracy is an adjustment of numbers of significant figures of numeric values of input data including variables.

6. A computer-readable storage medium storing a program for verifying an accuracy for model parameters computation, wherein the program causes a computer to perform a process comprising:

reading a model represented by difference equations from a storage apparatus;

computing difference equations that use numeric values of a time-series by replacing variables of the model with numeric values of a time-series that are stored in the storage apparatus;

preparing first constraint equations by implementing, to the difference equations using the numeric values of a time-series, error variables corresponding to the difference equations;

preparing second constraint equations including inequality equations in which a maximum value of an absolute value of each of the implemented error variables is set as an emax value;

determining the emax value by applying a quantifier elimination method to constraint equations including the first and the second constraint equations;

obtaining third constraint equations by substituting the emax value into the second constraint equations;

determining ranges of parameters of the model by applying a quantifier elimination method to constraint equations including the first and the third constraint equations;

comparing the determined ranges of parameters of the model with model parameter input values of the read model and verifying whether the determined ranges fall within a predetermined range of a degree of accuracy; and upon the ranges not falling within the accuracy range according to the verification result, repeating the reading the model, the computing difference equations, the preparing the first constraint equations, the preparing the second constraint equations, the determining the emax value, the obtaining the third constraint equations, the determining ranges of parameters, and the comparing the range of parameter after executing a processing of enhancing a degree of computation accuracy, wherein the processing of enhancing the degree of computation accuracy is a change of numerical solving methods of differential equations.

7. A computer-readable storage medium storing a program for verifying an accuracy for model parameters computation, wherein the program causes a computer to perform a process comprising:

reading a model represented by difference equations from a storage apparatus;

computing difference equations by replacing variables of the model with numeric values at one time among numeric values of a time-series that are stored in the storage apparatus;

preparing first constraint equations by implementing, to the difference equations using the numeric values of a time-series, error variables corresponding to the difference equations;

preparing second constraint equations including inequality equations in which a maximum value of an absolute value of each of the implemented error variables is set as an emax value;

determining the emax value by applying a quantifier elimination method to constraint equations including the first and the second constraint equations;

obtaining third constraint equations by substituting the emax value into the second constraint equations;

determining ranges of values of variables of the model at a time that are different from the one time by applying a quantifier elimination method to constraint equations including the first and the third constraint equations;

verifying numbers of significant figures that show a degree of computation accuracy of variable values by the determined ranges of variable values of the model; and upon a degree of computation accuracy of the variable values being verified as less than a predetermined degree by the verification of numbers of significant figures, repeating operations in and after the reading the model after executing a processing of enhancing the degree of computation accuracy, wherein the processing of enhancing the degree of computation accuracy is an adjustment of numbers of significant figures of numeric values of input data including variables.

8. A method of verifying an accuracy for model parameters computation; comprising:

reading a model represented by difference equations from a storage apparatus;

computing difference equations that use numeric values of a time-series by replacing variables of the model with numeric values of a time-series that are stored in the storage apparatus;

preparing first constraint equations by implementing, to the difference equations using the numeric values of a time-series, error variables corresponding to the difference equations;

preparing second constraint equations including inequality equations in which a maximum value of an absolute value of each of the implemented error variables is set as an emax value;

determining the emax value by applying a quantifier elimination method to constraint equations including the first and the second constraint equations;

obtaining third constraint equations by substituting the emax value into the second constraint equations;

determining ranges of parameters of the model by applying a quantifier elimination method to constraint equations including the first and the third constraint equations;

verifying numbers of significant figures that show a degree of computation accuracy of model parameters by the determined ranges of parameters of the model; and upon a degree of computation accuracy of the model parameters being verified as less than a predetermined degree by the verification of numbers of significant figures, repeating operations in and after the reading the model after executing a processing of enhancing the degree of computation accuracy, wherein the processing of enhancing the degree of computation accuracy is an adjustment of numbers of significant figures of numeric values of input data including variables.

9. An apparatus for verifying an accuracy for model parameters computation; comprising:

a reading unit to read a model represented by difference equations from a storage apparatus;

a computing unit to compute difference equations that use numeric values of a time-series by replacing variables of the model with numeric values of a time-series that are stored in the storage apparatus;

a first preparing unit to prepare first constraint equations by implementing, to the difference equations using the numeric values of a time-series, error variables corresponding to the difference equations;

a second preparing unit to prepare second constraint equations including inequality equations in which a maximum value of an absolute value of each of the implemented error variables is set as an emax value;

a first determining unit to determine the emax value by applying a quantifier elimination method to constraint equations including the first and the second constraint equations;

an obtaining unit to obtain third constraint equations by substituting the emax value into the second constraint equations;

a second determining unit to determine ranges of parameters of the model by applying a quantifier elimination method to constraint equations including the first and the third constraint equations;

a verifying unit to verify numbers of significant figures that show a degree of computation accuracy of model parameters by the determined ranges of parameters of the model; and a computation accuracy enhancement unit to enhance the degree of computation accuracy of the model parameters when the degree of computation accuracy of the model parameters is verified as less than a predetermined degree by the verification of numbers of significant figures, and to repeat operations in and after the reading the model operated by the reading unit, the computing unit, the first preparing unit the second preparing unit, the first determining unit, the obtaining unit, the second determining unit, and the verifying unit after enhancing the degree of computation accuracy, wherein the computation accuracy enhancement unit enhances the degree of computation accuracy by adjusting numbers of significant figures of numeric values of input data including variables.

10. An apparatus for verifying an accuracy for model parameters computation; comprising:

reading means to read a model represented by difference equations from a storage apparatus;

computing means to compute difference equations that use numeric values of a time-series by replacing variables of the model with numeric values of a time-series that are stored in the storage apparatus;

first preparing means to prepare first constraint equations by implementing, to the difference equations using the numeric values of a time-series, error variables corresponding to the difference equations;

second preparing means to prepare second constraint equations including inequality equations in which a maximum value of an absolute value of each of the implemented error variables is set as an emax value;

first determining means to determine the emax value applying a quantifier elimination method to constraint equations including the first and the second constraint equations;

obtaining means to obtain third constraint equations by substituting the emax value into the second constraint equations;

second determining means to determine ranges of parameters of the model by applying a quantifier elimination method to constraint equations including the first and the third constraint equations;

verifying means to verify numbers of significant figures that show a degree of computation accuracy of model parameters by the determined ranges of parameters of the model; and computation accuracy enhancement means to enhance the degree of computation accuracy of the model parameters when the degree of computation accuracy of the model parameters is verified as less than a predetermined degree by the verification of numbers of significant figures, and to repeat operations in and after the reading the model operated by the reading means, the computing means, the first preparing means, the second preparing means, the first determining means, the obtaining means, the second determining means, and the verifying means after enhancing the degree of computation accuracy, wherein the computation accuracy enhancement means enhances the degree of computation accuracy by adjusting numbers of significant figures of numeric values of input data including variables.

\* \* \* \* \*

UNITED STATES PATENT AND TRADEMARK OFFICE
CERTIFICATE OF CORRECTION

| | |
|---|---|
| PATENT NO. | : 7,711,528 B2 |
| APPLICATION NO. | : 11/237661 |
| DATED | : May 4, 2010 |
| INVENTOR(S) | : Shigeo Orii et al. |

It is certified that error appears in the above-identified patent and that said Letters Patent is hereby corrected as shown below:

Title page Column 2 (Other Publications), Line 5, change "Transduers" to --Transducers--.

Title page Column 2 (Other Publications), Line 12, change "Quanitifier" to --Quantifier--.

Title page Column 2 (Other Publications), Line 14, change "SpringerWeinNewYork" to --Springer, Wein, New York--.

Column 13, Line 5, change "equation;" to --equations;--.

Column 14, Line 26, change "equation;" to --equations;--.

Column 14, Line 32, change "failing" to --falling--.

Column 17, Line 25-26, change "emax value applying" to --emax value by applying--.

Signed and Sealed this

Twenty-fourth Day of August, 2010

David J. Kappos
*Director of the United States Patent and Trademark Office*